(12) United States Patent
Doty

(10) Patent No.: US 8,444,598 B2
(45) Date of Patent: May 21, 2013

(54) INTRAVASCULAR THERAPEUTIC AGENT DELIVERY

(75) Inventor: David Doty, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2597 days.

(21) Appl. No.: 11/215,590

(22) Filed: Aug. 29, 2005

(65) Prior Publication Data

US 2007/0060883 A1 Mar. 15, 2007

(51) Int. Cl.
*A61M 31/00* (2006.01)

(52) U.S. Cl.
USPC .................................. 604/103.04; 604/104

(58) Field of Classification Search
USPC .................. 604/96.01, 103.04, 104
See application file for complete search history.

(56) References Cited

U.S. PATENT DOCUMENTS

| | | | |
|---|---|---|---|
| 4,351,341 A | 9/1982 | Goldberg et al. | |
| 4,459,977 A | 7/1984 | Pizon et al. | |
| 4,531,936 A | 7/1985 | Gordon | |
| 4,689,041 A | 8/1987 | Corday et al. | |
| 4,850,969 A | 7/1989 | Jackson | |
| 4,960,410 A | 10/1990 | Pinchuk | |
| 5,033,998 A | 7/1991 | Corday et al. | |
| 5,423,744 A | 6/1995 | Gencheff et al. | |
| 5,460,608 A | 10/1995 | Lodin et al. | |
| 5,586,982 A | 12/1996 | Abela | |
| 5,649,908 A | 7/1997 | Itoh | |
| 5,833,650 A | 11/1998 | Imran | |
| 5,873,852 A | 2/1999 | Vigil et al. | |
| 5,908,407 A | 6/1999 | Frazee et al. | |
| 6,165,152 A | 12/2000 | Becker et al. | |
| 6,193,685 B1 | 2/2001 | Goodin | |
| 6,398,757 B1 | 6/2002 | Varenne et al. | |
| 6,409,716 B1 | 6/2002 | Sahatjian et al. | |
| 6,482,171 B1 * | 11/2002 | Corvi et al. | 604/96.01 |
| 6,605,074 B2 | 8/2003 | Zadno-Azizi et al. | |
| 6,616,650 B1 | 9/2003 | Rowe | |
| 6,881,201 B1 | 4/2005 | Duchamp | |
| 7,488,337 B2 * | 2/2009 | Saab et al. | 606/192 |
| 2002/0062119 A1 * | 5/2002 | Zadno-Azizi | 604/509 |
| 2002/0169414 A1 | 11/2002 | Kletschka | |
| 2002/0173817 A1 | 11/2002 | Kletschka et al. | |
| 2003/0009190 A1 | 1/2003 | Kletschka et al. | |
| 2003/0055401 A1 * | 3/2003 | Larson et al. | 604/527 |
| 2003/0078562 A1 | 4/2003 | Makower et al. | |
| 2003/0181843 A1 | 9/2003 | Bibber et al. | |
| 2003/0225434 A1 * | 12/2003 | Glantz et al. | 606/194 |
| 2004/0143240 A1 * | 7/2004 | Armstrong et al. | 604/528 |
| 2005/0043680 A1 * | 2/2005 | Segal et al. | 604/104 |

FOREIGN PATENT DOCUMENTS

| | | |
|---|---|---|
| EP | 0254885 | 2/1988 |
| WO | WO99/25421 | 5/1999 |

* cited by examiner

*Primary Examiner* — Theodore Stigell
*Assistant Examiner* — Gerald Landry, II

(57) ABSTRACT

Intravascular devices and a method of delivering at least one therapeutic agent. The device includes an elongate element with proximal and distal portions and at least first and second lumens provided therein. The first lumen is adapted for delivering at least one therapeutic agent. The second lumen is adapted for allowing fluid therethrough. An expandable member is disposed adjacent to the distal portion of the elongate element. At least one tip cut is provided in a distal tip portion of the elongate element. The at least one tip cut is adapted for providing flexibility to the elongate element. The method includes providing an elongate element. Spacing of at least one tip cut is varied during positioning of the elongate element within a vessel. The vessel is occluded with the elongate element. The at least one therapeutic agent is delivered to tissue adjacent the occluded vessel.

7 Claims, 6 Drawing Sheets

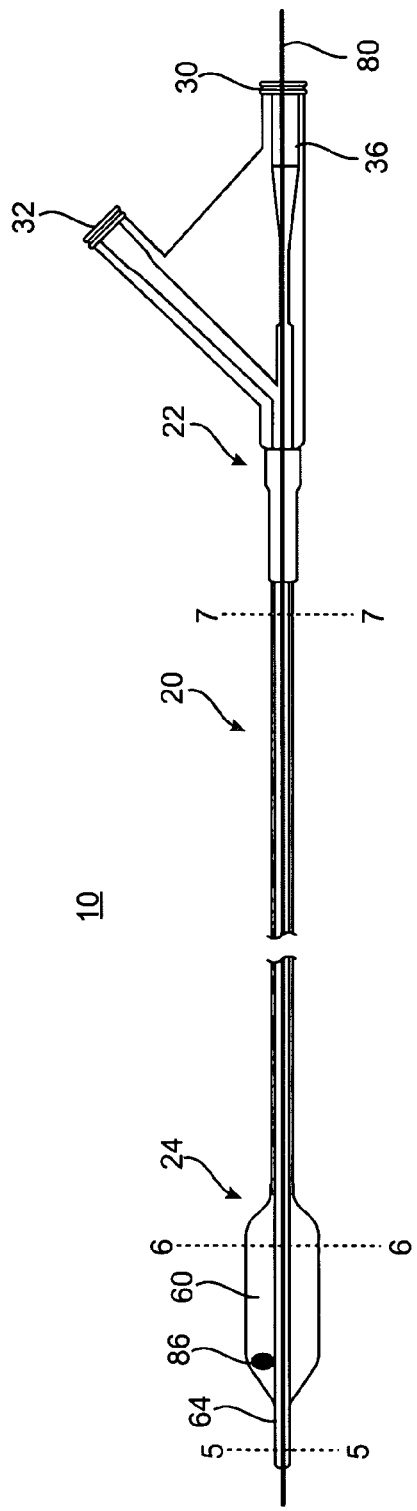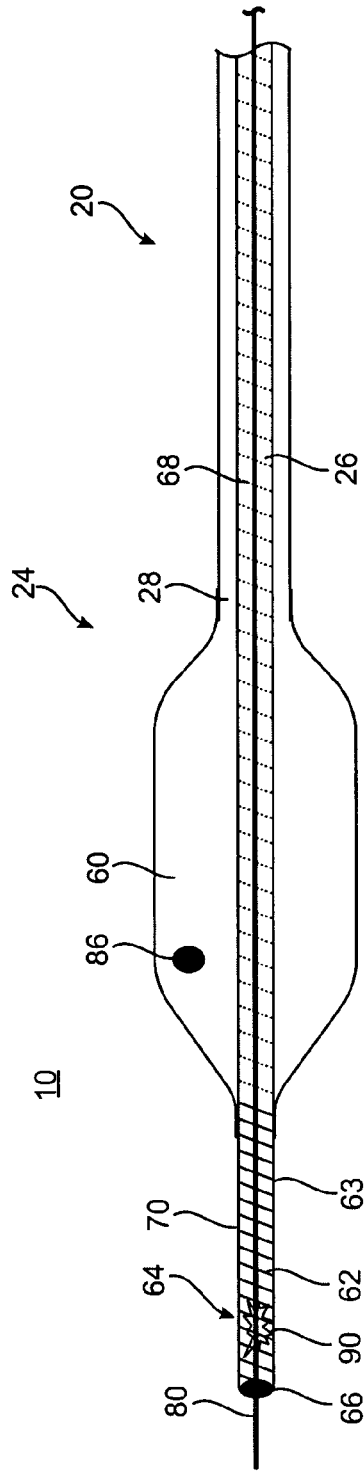

INTRAVASCULAR THERAPEUTIC AGENT DELIVERY

TECHNICAL FIELD OF THE INVENTION

The present invention relates generally to the field of vascular medical devices. More particularly, the invention relates to an intravascular therapeutic agent delivery device and a method of delivering at least one therapeutic agent.

BACKGROUND OF THE INVENTION

Coronary artery disease (CAD) results from arteriosclerosis of blood vessels serving the heart. Arteriosclerosis is a hardening and narrowing of the arteries commonly accompanied by a deposition of waxy substance therein. This substance, known as plaque, is made of cholesterol, fatty compounds, calcium, and the blood-clotting material fibrin. Often the arteries of the heart can suddenly become so severely blocked that there is an inadequate blood supply after the blockage, leading to the occurrence of a myocardial infarction or heart attack. Although some heart attacks are caused by such "hard" plaques, many are caused by "soft" or vulnerable plaques. A vulnerable plaque is an inflamed part of an artery that can burst. This can lead to the formation of a blood clot, which can reduce or block the flow of blood.

Soon after a myocardial infarction, the area of cardiac tissue downstream the blockage may suffer damage. The damage is caused by a lack of adequate blood flow, known as ischemia, as the tissue is starved of oxygen and nutrients. Unless the blockage is resolved relatively quickly, the ischemic cells may begin to die. Often, a surgical procedure, such as a Coronary Artery By-Pass Grafting (CABG), is used to graft new blood vessels to the ischemic area to improve circulation. Alternatively, a Percutaneous Transluminal Coronary Angioplasty (PTCA) procedure optionally accompanied by stenting of the blocked vessel is performed to reopen the vessel and maintain blood flow. However, by-passing or reopening of the arteries is sometimes not possible or at least not immediately possible because of limitations of present methodologies, risk to the patient from surgical intervention, or other circumstances. In certain instances, it may be preferable to treat the heart condition by utilizing the cardiac venous system, which generally runs parallel to or adjacent to the coronary arteries.

One therapy for limiting or reducing myocardial damage during or after a heart attack involves a localized delivery of therapeutic agent(s) to the heart tissue. The therapeutic agents include gene therapy agents, which have recently emerged as a powerful approach to treating a variety of diseases. The direct transfer of genetic material into myocardial tissue in vivo has been demonstrated for expressing various proteins. Engineered and stem cell therapies have also shown promise. The therapeutic agents may also include drug agents. The expressed proteins and drug agents may have various therapeutic benefits for improving circulation/angiogenesis, limiting ongoing tissue damage, preventing future tissue damage, repairing damaged tissue, and the like.

The localized delivery of therapeutic agents to a specific treatment site, such as the heart, represents a substantial challenge in the design of delivery systems. An approach to accomplish site-specific drug delivery involves the use of a catheter or like device, which can be advanced through the vasculature and positioned at a treatment site. The catheter provides localized delivery of drug from a location that may be some distance from the treatment site (i.e., outside the body of the patient). For example, a blocked artery may prevent blood from flowing downstream into its corresponding vein. As such, accessing the blockage from the venous direction provides a viable treatment option.

One consideration for catheter design relates to its maneuverability. The advancement of the catheter through the sometimes tortuous vasculature requires a relatively flexible device. A maneuverable catheter may reduce the time and skill needed to advance the apparatus to the treatment site. In addition, a maneuverable catheter may be less likely to contact the vascular tissue during its advancement therefore minimizing trauma to the vessels. Another consideration in the design of catheters used for therapeutic agent delivery relates to those devices used for long-term agent delivery (e.g., several hours to several days, weeks, or months). Long-term therapeutic agent delivery requires that such catheters do not occlude the blood flow for an extended period of time, thereby allowing downstream tissue to receive an adequate blood supply.

Accordingly, it would be desirable to provide a strategy for intravascularly delivering therapeutic agents that would overcome the aforementioned and other limitations.

SUMMARY OF THE INVENTION

A first aspect according to the invention provides an intravascular device. The device includes an elongate element with proximal and distal portions and at least first and second lumens provided therein. The first lumen is adapted for delivering at least one therapeutic agent. The second lumen is adapted for allowing fluid flow therethrough. An expandable member is disposed adjacent to the distal portion of the elongate element and operably attached to the second lumen. At least one tip cut is provided in a distal tip portion of the elongate element. The at least one tip cut is adapted for providing flexibility to the elongate element.

A second aspect according to the invention provides a method of delivering at least one therapeutic agent. The method includes providing an elongate element including at least one tip cut positioned adjacent a distal tip portion of the elongate element. The at least one tip cut provides flexibility to the elongate element. Spacing of the at least one tip cut is varied during positioning of the elongate element within a vessel. The vessel is occluded with the elongate element. The at least one therapeutic agent is delivered to tissue adjacent the occluded vessel.

A third aspect according to the invention provides an intravascular device. The device includes an elongate element including at least one tip cut positioned adjacent a distal tip portion of the elongate element. The at least one tip cut provides flexibility of the elongate element. The device further includes means for varying spacing of the at least one tip cut during positioning of the elongate element within a vessel, means for occluding the vessel with the elongate element, and means for delivering the at least one therapeutic agent to tissue adjacent the occluded vessel.

The foregoing and other features and advantages of the invention will become further apparent from the following description of the presently preferred embodiments, read in conjunction with the accompanying drawings. The drawings have not been drawn to scale. The detailed description and drawings are merely illustrative of the invention, rather than limiting the scope of the invention being defined by the appended claims and equivalents thereof.

BRIEF DESCRIPTION OF THE DRAWINGS

FIG. 1 illustrates an intravascular device in accordance with a first embodiment of the present invention;

FIG. 2 illustrates a detail view of a distal portion of the intravascular device shown in FIG. 1;

DESCRIPTION OF THE PRESENTLY PREFERRED EMBODIMENTS

Figure 3A:
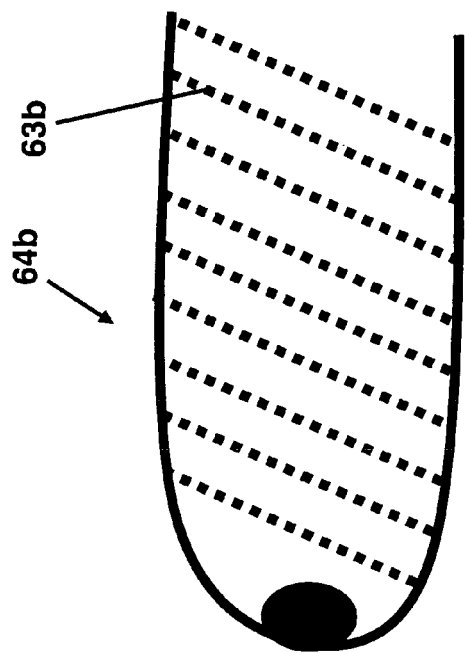
FIGS. 3A and 3B illustrate detail views of alternative distal tip embodiments in accordance with the present invention.

The following description relates primarily to the positioning and operation of an intravascular device for treating heart tissue (i.e., by delivering one or more therapeutic agents) of a patient after a myocardial infarction. The treatment may occur, for example, before, during, and/or after a CABG or PTCA procedure in an effort to salvage and/or rehabilitate myocardial tissue. Those skilled in the art will recognize that although the present invention is described primarily in the context of localized delivery of therapeutic agents in a coronary vein blood vessel with a specific intravascular device, the inventor contemplates numerous other applications and variations to the device.

For example, an intravascular device according to the invention may be deployed within another arterial or venous blood vessel, or adapted as an intraluminal device for use in another vessel such as the intestine, air duct, esophagus, bile duct, and the like. Any number of devices capable of performing the prescribed method(s) may be adapted for use with the present invention. Furthermore, the deployment strategies, treatment site and tissues, and therapeutic agents are not limited to those described. Numerous modifications, substitutions, additions, and variations may be made to the devices and methods while providing effective delivery of therapeutic agents in accordance with the present invention.

Referring to the drawings, wherein like reference numerals refer to like elements, FIGS. 1 and 2 illustrate an intravascular device in accordance with a first embodiment of the present invention, the device shown generally by numeral 10. Device 10 includes an elongate element 20 including a proximal portion 22 and a distal portion 24. In the present description and figures, the distal portion 22 of the elongate element 20 is advanced into the vasculature (preferably the venous system) of a patient to a treatment site. A segment of the proximal portion 24 remains outside of the body. Elongate element 20 further includes a first lumen 26 and a second lumen 28 formed therein. First lumen 26 is adapted for delivering therapeutic agents. Second lumen 28 is adapted for allowing fluid flow therethrough. An expandable member 60 is disposed adjacent to the distal portion 24 of the elongate element 20. A tip cut 62 is provided in a distal tip portion 64 of the elongate element 20. The tip cut 62 is adapted for providing flexibility to the elongate element 20. Those skilled in the art will recognize that the configuration of the elongate element, distal portion, lumen configuration and number, and tip cut may vary without departing from the spirit and scope of the present invention.

Elongate element 20 may be a tubular member, such as a catheter, having a substantially circular (in cross-section) inside and outside walls which are preferably substantially smooth. Catheters typically comprise tubes made of one or more polymeric materials, sometimes in combination with metallic reinforcement. In some applications (such as smaller, more tortuous vessels), it is desirable to construct the catheter from very flexible materials to facilitate advancement of the device into such difficult access locations. Catheters are known in the art that provide different regions of flexibility (i.e., a stiffer proximal section and a more flexible distal section). Elongate element 20 may be manufactured substantially from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® resin, Vestamid® resin, Tecoflex® resin, Halar® resin, Hyflon® resin, Pellathane® polyurethane, combinations thereof, and the like. In one embodiment, the elongate element 20 may be sized to permit access to small diameter veins and venules (e.g., 1.0-2.0 mm in diameter).

Elongate element 20 may include a two-arm Y Luer fitting 30, 32 positioned adjacent its proximal portion 22. Luer fitting 32 is fluidly connected to the second lumen 28 for facilitating expansion and compression of the expandable member 60. Luer fitting 30 may include a pressure relief valve 36, which allows drainage of coronary venous blood and fluids and may avoid the complications of hemorrhage, edema, thrombosis, and arrhythmias observed with prolonged increase of coronary sinus pressure. This is commonly known as pressure-controlled intermittent coronary sinus occlusion (PICSO). The sudden occlusion of a coronary artery may result in a significant decrease in coronary sinus pressure. By increasing coronary sinus pressure, PICSO may redistribute coronary venous flow to jeopardized areas of the myocardium distal to an arterial occlusion.

In FIG. 1, expandable member 60 is shown in an expanded position for providing vessel occlusion. The expandable member 60, when collapsed, provides a smaller profile size of the elongate element 20 to facilitate advancement through the vasculature to a treatment site. In one embodiment, the expandable member 60 may be a balloon. Balloons are known in the art for performing balloon type angioplasty, stent placement, vessel occlusion, and vessel repair/treatment procedures. The balloon may comprise a wide variety of inner structures, such as different lumen designs, including triple lumen, dual lumen and co-axial lumen. Varieties of internal structures and design variations are meant to be included herein. In another embodiment, the expandable member may be another expandable/compressible device or mechanism for slowing or stopping fluid flow through the vessel. Those skilled in the art will recognize that a number of strategies may be used for occluding a vessel in accordance with the present invention.

Expandable member 60 may be manufactured substantially from a resilient material such as polyethylene, polyethylene terephthalate (PET), polyurethane, polyvinyl chloride, polyolefin, nylon, Pebax® resin, Pellathane® polyurethane, Hytrel® thermoplastic polyester elastomers, combinations thereof, and the like. Elongate element 20 and/or expandable member 60 may include and/or be coated with a lubricious material to facilitate movement (i.e., reduce friction) through the vascular system. Examples of such coatings include silicone and more preferably hydrophilic coatings involving hydrogel polymers or the like, such as polymer networks of a vinyl polymer and an uncrosslinked hydrogel.

Distal tip portion 64 may be shaped (e.g., rounded) and/or manufactured from a resilient material to reduce harm from inadvertent contact with a vessel wall while it is being advanced through the vasculature. A guidewire 80 may be received by Luer fitting 30, positioned through the first lumen 26, and exit through an aperture 66 positioned at the distal tip portion 64. As such, the elongate element 20 may be slidably guided and advanced via the guidewire 80 that is pre-positioned through the vasculature at the treatment site. First lumen 26 is preferably larger in diameter than the guidewire 80 thereby providing a gap for a fluid to flow. In one embodiment, therapeutic agent(s) may be delivered to the distal tip 64 via the first lumen 26. In another embodiment, venous blood may flow proximally up the first lumen 26 and to the Luer fitting 30.

Figure 3B:
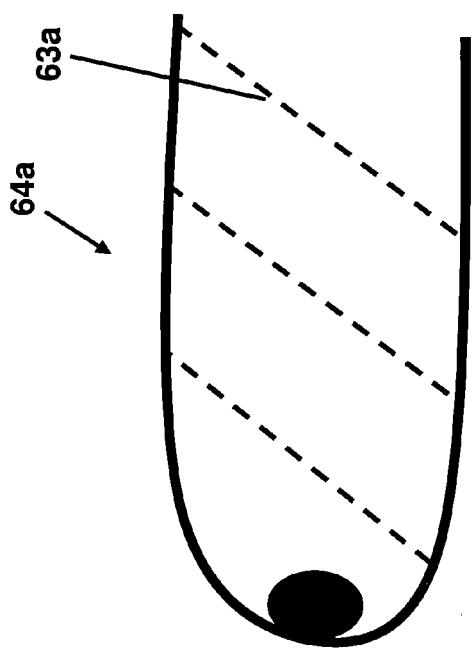

In one embodiment, the tip cut 62 may be formed by completely scoring the distal tip 64 material as a spiral cut 63, extending from the distal tip 64 to a distal end of the expandable member 60. Spiral cut 63 may vary in fineness (i.e., width), pitch angle, density, geometry, and the like to influence the flexibility of the distal tip 64. For example, the flexibility of the distal tip 64 will increase with a less fine and a smaller pitch angle (i.e., the pitch of the spiral formed by the cut). In FIG. 3A, distal tip 64a includes spiral cuts 63a that are finer and have a smaller pitch angle (i.e., less dense) than distal tip 64b spiral cuts 63b, which is shown in FIG. 3B. As such, the distal tip 64a is relatively less flexible than the distal tip 64b.

Figure 4:
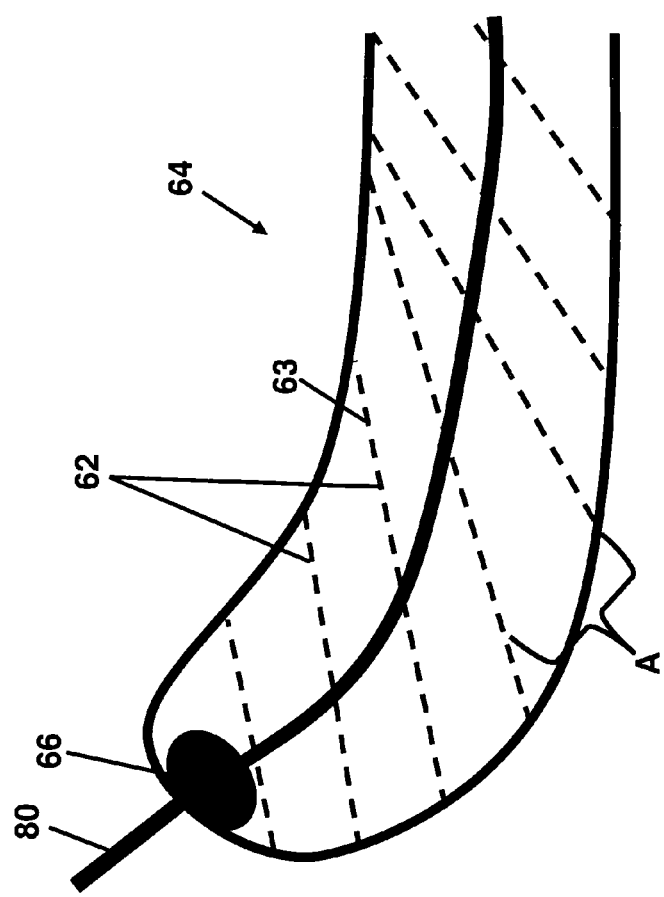
FIG. 4 illustrates a detail view of a distal tip bending during positioning the intravascular device shown in FIG. 1.

During positioning of the elongate element 20, spacing A of the tip cuts 62 varies relative one to another, as shown in FIG. 4. Specifically, as the elongate element 20 is advanced through the vasculature and encounters a curvature on the guidewire 80, the distal tip 64 follows the curve thereby changing the space A between the cuts 62 one relative to another. Those skilled in the art will recognize that the tip cut(s) 62 and shaft cut(s) 68 may include many different shapes, sizes, numbers, configurations, combinations thereof, and the like and are not limited to the examples described and illustrated herein. In addition, the shaft cut(s) are not limited to any positioning on the elongated element 20.

Referring again to FIG. 2, a sleeve 70 may be positioned over the portion of the elongated element 20 including cut portions to prevent any contents from entering or leaving the elongated element 20. Preferably, the sleeve is manufactured from a thin, impermeable, flexible material. Tip cut 62 may continue past the distal tip 64 as a shaft cut 68 to provide flexibility to the elongate element 20. In some applications, it is desirable to provide a catheter-like device with a relatively stiff proximal section and a flexible distal section to maximize both maneuverability and pushability. As such, the shaft cut 68 may be configured to become more flexible from the proximal portion 22 moving toward the distal portion 24. This may be accomplished by, for example, varying the pitch angle of the shaft cut 68 and/or by other strategies known in the art (i.e., metallic reinforcements, stiffeners, wall thickness, etc.). A flexing member 90 may be operably attached to the elongate member 20 adjacent the distal tip portion 64. Flexing member 90 may be, for example, a spring, a coil, or additional material associated with the distal tip portion 64 for customizing the flexibility (i.e., add a degree of stiffness) adjacent the distal tip portion 64.

Figure 7:
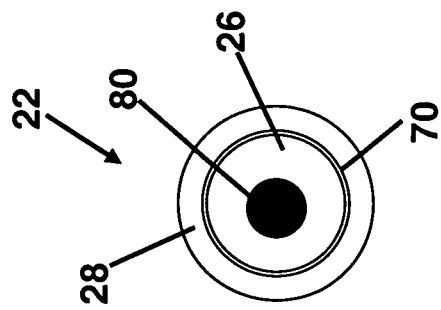
FIG. 7 is a transverse sectional illustration of the intravascular device shown in FIG. 2, taken along the line 7-7.
Figure 6:
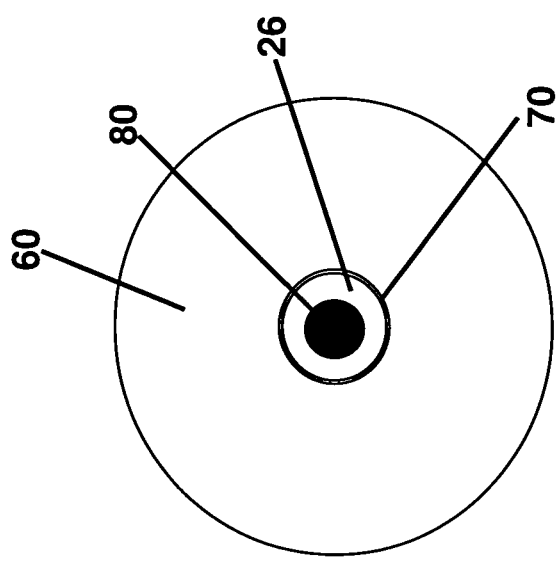
FIG. 6 is a transverse sectional illustration of the intravascular device shown in FIG. 2, taken along the line 6-6.
Figure 5:
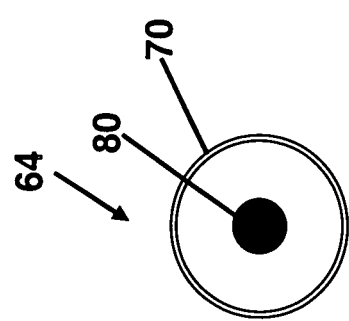
FIG. 5 is a transverse sectional illustration of the intravascular device shown in FIG. 2, taken along the line 5-5.

FIGS. 5, 6, and 7 are transverse sectional illustrations of the intravascular device 10 shown in FIG. 1, taken along the lines 5-5, 6-6, and 7-7, respectively. The relative positions of the first lumen 26, second lumen 28, expandable member 60, sleeve 70, and guidewire 80 are shown. Those skilled in the art will recognize that the components and their relative positions may vary without departing from the spirit and scope of the present invention.

Figure 8:
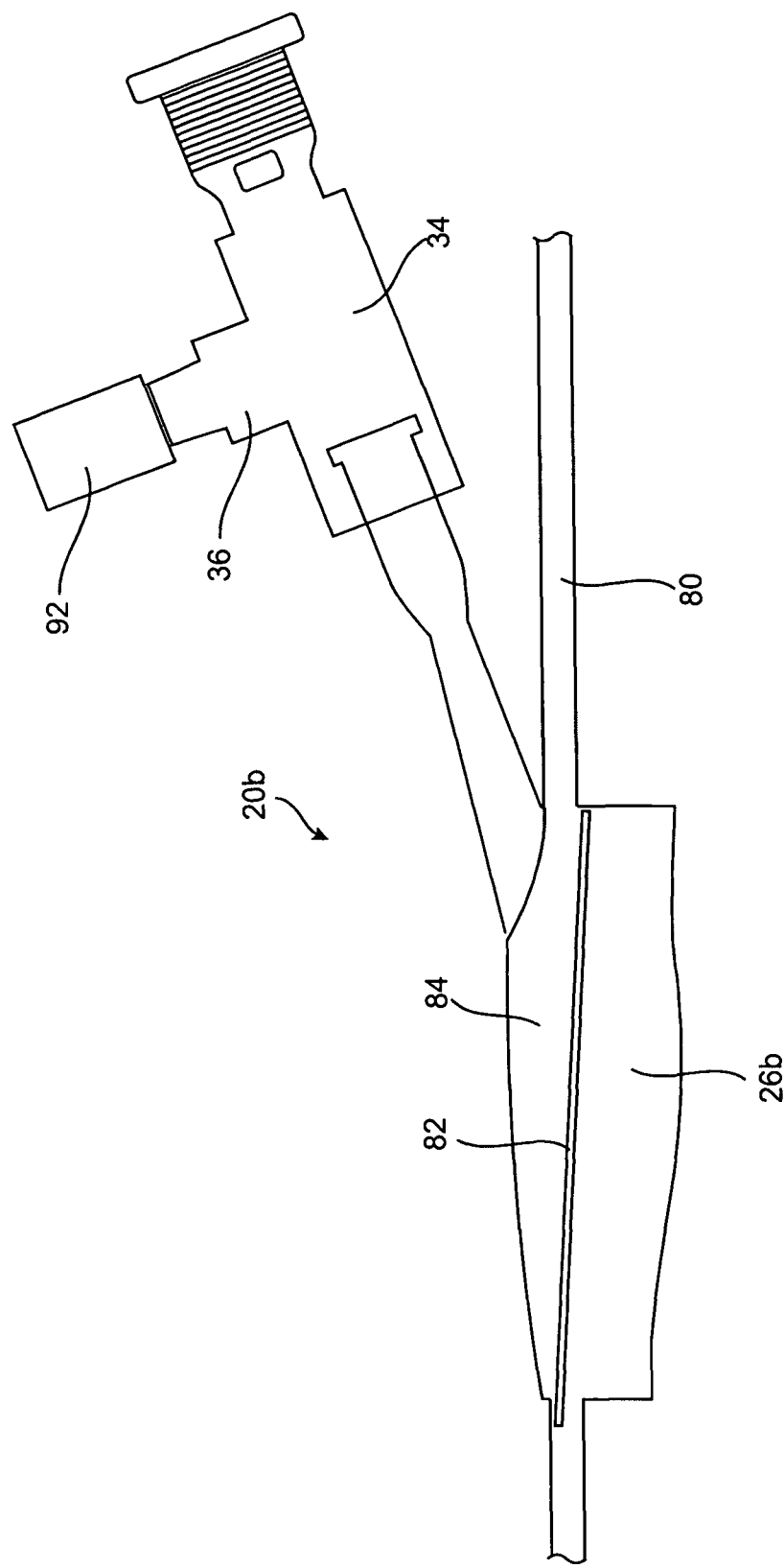
FIG. 8 illustrates an intravascular device in accordance with a second embodiment of the present invention.

In a second embodiment, shown in FIG. 8, elongate element 20b may include a longitudinal guide way 82 to provide transverse access of the guidewire 80 to the first lumen 26b. Longitudinal guide way 82 may be formed from a pair of separable flaps that normally close together to define the first lumen 26b. Guidewire 80 may be inserted or removed through first lumen 26b, while a guide member 84 is held stationary with respect to the elongate element 20b. In this fashion, the guidewire 80 can be exchanged within the elongate element 20b. In yet another type of manipulation, the guidewire 80 and elongate element 20b may be held relatively still while the guide member 84 is translocated, thus unzipping and zipping the guidewire 80 and elongate element 20b transversely apart or together, depending on which direction guide member 84 is moved.

Figure 9:
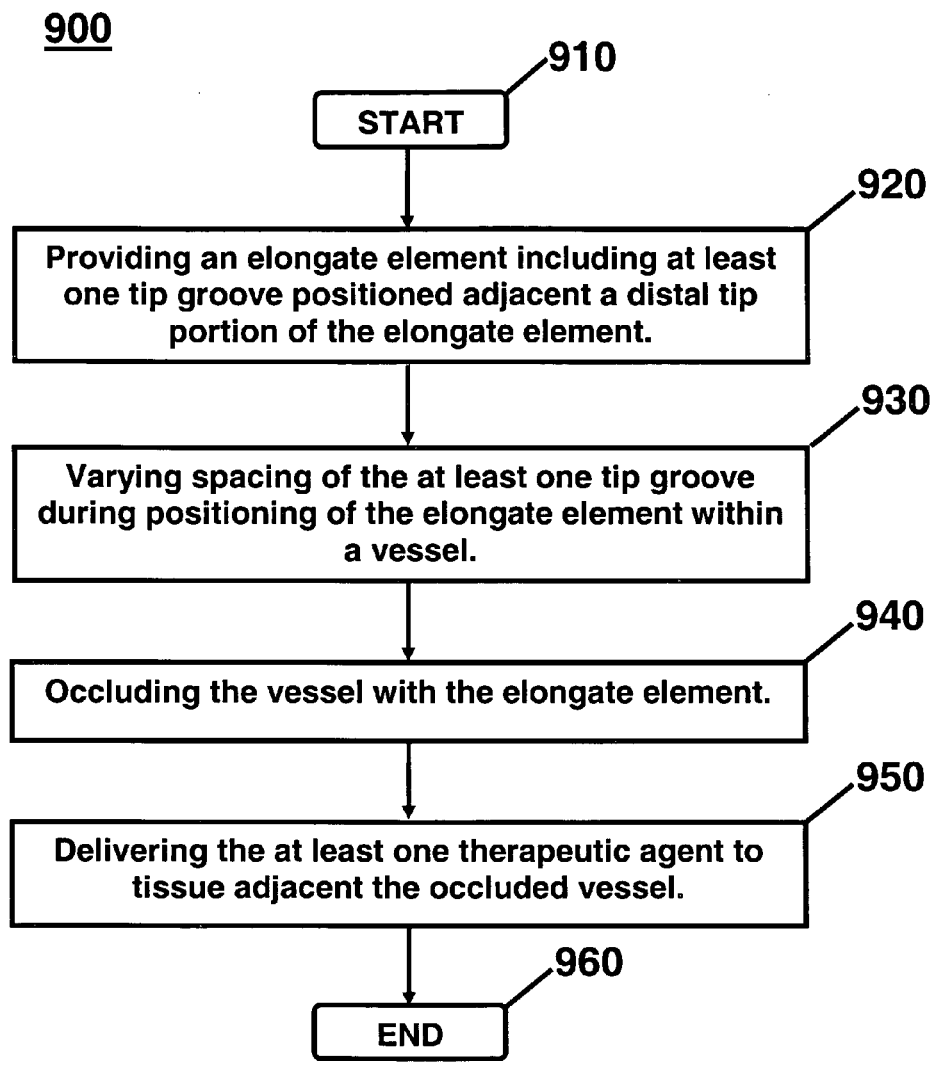
FIG. 9 illustrates a flowchart of a method of delivering at least one therapeutic agent, in accordance with the present invention.

FIG. 9 illustrates a flowchart of a method 100 representative of a method of delivering at least one therapeutic agent, in accordance with the present invention. Method 900 begins at step 910. At step 920, an elongate element including at least one tip groove positioned adjacent a distal tip portion of the elongate element is provided. The at least one tip groove provides flexibility to the elongate element.

At step 930, spacing of the tip cut 62 is varied during positioning of the elongate element 20 within the vessel. In one embodiment, the elongate member 20 is inserted through a percutaneous venous entry, such as through the jugular vein, and the distal tip 64 is maneuvered through a vessel pathway to the right atrium of the heart into the coronary sinus. The coronary sinus is drained into by a number of smaller veins, typically, from left to right along its course, the great cardiac vein, the oblique vein of the left atrium, the posterior vein of the left ventricle, the middle cardiac vein, and the small cardiac veins. If necessary, a smaller vein may be accessed from the coronary sinus. Elongate element 20 may be advanced along a pre-positioned guidewire 80 to access the treatment site through the vessel pathway. Those skilled in the art will recognize that the entry point, vessel pathway, and treatment site may vary and is contingent upon many factors including the region of the heart or other tissue requiring treatment. The tip cuts 62 facilitate maneuverability and positioning of the elongate element 20 through a vessel pathway.

The positioning of the elongate element 20 may be aided by visualization methods known in the art, such as fluoroscopy and/or intravascular ultrasound (IVUS). Elongate element 20 may include one or more radiopaque markers 86 to enhance the positioning process. The radiopaque material may comprise barium sulfate, gold, silver, tantalum oxide, tantalum, platinum, platinum/iridium alloy, tungsten, and other materials typically used to assist intravascular device positioning.

At step 940, the vessel is occluded with the elongate element 20. In one embodiment, the expandable member 60 may be inflated by flowing a fluid, such as a radiopaque contrast liquid, into the interior of the expandable member 60 through the second lumen 28. Expandable member 60 may be expanded until it contacts the vessel wall to achieve vessel occlusion. Preferably the inflation is performed with a relatively low inflation pressure so as not to damage or rupture the vessel. Further, the expansion pressure of the expandable member 60 may be monitored. The expandable member 60 may be expanded with one or more operators and/or a device, such as an indeflator device adapted for such a purpose, as known in the art. The expandable member 60 need not provide an absolute occlusion of the vessel.

At step 950, at least one therapeutic agent is administered to tissue adjacent the occluded vessel. As coronary veins generally run parallel to or at least adjacent to coronary arteries, administration of the therapeutic agent into a vein permits concomitant administration of the agent to the diseased artery, In one embodiment, one or more therapeutic agents are administered through the first lumen 26, out of the aperture 66 of the distal tip 64, and into the venous blood vessel. The therapeutic agent may be delivered retrogradely to the treatment site through its adjoining coronary veins in a direction opposite to the normal outflow of venous blood through that vein. The therapeutic agent(s) may cross from the coronary veins into the tissue capillary circulation (i.e., as microcirculation) to provide treatment to the heart tissue. As the blood vessel is temporarily occluded by the expandable member 60, the therapeutic agent(s) is/are not carried away by blood flow thereby creating a therapeutic agent reservoir. As such, the therapeutic agent(s) is/are more likely to act on the tissue and/or penetrate the relatively fine venous epithelia and into the tissue of the treatment site. In another or the same embodiment, the therapeutic agent(s) may be delivered under slight pressure to augment uptake by the surrounding tissue.

In one embodiment, the therapeutic agent may be a gene therapy agent or a drug agent such as an antiangiogenesis agent, antiarteriosclerotic agent, antiarythmic agent, antibiotic, antibody, anticoagulant, antidiabetic agent, antiendothelin agent, antihypertensive agent, antiinflammatory agent, antimitogenic factors, antineoplastic agent, antioxidants, antiplatelet agent, antipolymerases, antiproliferative agent, antirestenotic drug, antisense agent, antithrombogenic agent, calcium channel blockers, chemotherapeutic agent, clot dissolving agent, fibrinolytic agent, growth factor, growth factor inhibitor, immunosuppressant, nitrate, nitric oxide releasing agent, remodeling inhibitors, vasodilator, agent having a desirable therapeutic application, and the like. Specific examples of gene therapy agents include a recombinant DNA product, a recombinant RNA product, stem cells, engineered or altered cells, and a virus mediated gene therapy agent. Specific example of drugs include abciximab, angiopeptin, calcium channel blockers, colchicine, eptifibatide, heparin, hirudin, lovastatin, methotrexate, streptokinase, taxol, ticlopidine, tissue plasminogen activator, steroid, trapidil, urokinase, vasodilators, vasospasm inhibitors, and growth factors VEGF, TGF-beta, IGF, PDGF, and FGF.

In another or the same embodiment, the therapeutic agent may be substance(s) that reduce tissue ischemia. This may be necessary in instances when surgical intervention is not immediately possible to repair damage from a myocardial infarction. A retroperfusion procedure may be performed via administration of therapeutic agent(s) through the first lumen 26. Coronary retroperfusion limits or reduces myocardial damage when administered as a preemptive or remedial treatment, or both. Retroperfusion may also be effective therapy when targeted to slow or, in some cases, reverse the progression from myocardial ischemia to the irreversible damage associated with myocardial infarction.

Retroperfusion may employ an autologous sanguinous solution, such as venous or arterial blood or a solution including blood, or an extrinsic asanguinous solution, such as artificial serum, an oxygenated or non-oxygenated crystalloid plasmatic solution, a solution including aspartate or glutamate, or other tissue enhancement solution. Suitable tissue enhancing solutions have a normal pH of about 7.4 and an oncotic pressure approximately equal to that of blood and may contain buffers (e.g., bicarbonate) to modify the acidity present in the ischemic tissue and membrane stabilizing additives, such as lidocaine or magnesium. Such solutions may reduce harm to endothelia and may speed recovery after more complete revascularization, such as by PTCA or CABG, and thereby permit physicians to maximize myocardial salvage.

After delivery of the therapeutic agent(s), the expandable member 60 may be compressed. In one embodiment, compression may be achieved by slowly withdrawing fluid from the expandable member 60 via the second lumen 32. Elongate element 20 may then be withdrawn from the patient along with the guidewire 80. In another embodiment, the guidewire 80 may be left in place for repeated treatment(s) with the device 10. In such an instance, the elongate element 20 would be removed from the patient and reinserted along the pre-positioned guidewire 80 at a later time when another treatment was required. In yet another embodiment, the elongate element 20 may be left in place after the expandable member 60 has been compressed to allow blood or other fluids to flow through the vessel. The intermittent expansion-compression cycle of the expandable member 60 also enhances the washout of toxic metabolites that form during periods of coronary occlusion and ischemia. The expandable member 60 may then be re-expanded at a later time to allow repeat treatment(s). The treatment(s) may be repeated over several time periods (e.g. minutes, hours, days, etc.).

In the second embodiment, as shown in FIG. 8, the venous blood at the treatment site may assessed at various points of the treatment procedure by monitoring the flow of blood flowing proximally up the first lumen 26 and to a Touhy-Borst adapter 34. A monitor 92 may be operably attached to the Touhy-Borst adapter 34 to determine characteristics of the blood flowing through the second lumen. The characteristics may include blood flow rate, blood pressure, blood oxygenation, therapeutic agent concentration, indicators of the treatment procedure, and the like. Such characteristics may provide insight into the next course of action required for treatment.

The method may end at step 960 and repeated as necessary at the same or another treatment site.

While the embodiments of the invention disclosed herein are presently considered to be preferred, various changes and modifications may be made without departing from the spirit and scope of the invention. The intravascular device and method of delivering at least one therapeutic agent of the present invention are not limited to any particular design, configuration, methodology, or sequence. For example, the elongate element, expandable member, lumens, therapeutic agents, distal tip portion, tip cut, and treatment site may vary without limiting the utility of the invention. Furthermore, the described order may vary and may include additional steps to provide effective stent deployment Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. A method of delivering at least one therapeutic agent, the method comprising:
providing an elongate element comprising a polymer and including at least one tip cut in the polymer positioned adjacent a distal tip portion of the elongate element, the at least one tip cut providing flexibility to the elongate element;

varying spacing between longitudinally adjacent portions of a single tip cut or between longitudinally adjacent tip cuts during positioning of the elongate element within a vessel;

occluding the vessel with the elongate element to produce an occluded vessel; and delivering the at least one therapeutic agent to tissue adjacent the occluded vessel.

2. The method of claim 1 wherein the at least one therapeutic agent is administered under pressure.

3. The method of claim 1 further comprising providing transverse guidewire access to the elongate element.

4. The method of claim 1 further comprising providing a flexing member adjacent a distal tip portion of the elongate element.

5. The method of claim 1 further comprising repeating delivery of at least one therapeutic agent to the tissue adjacent the occluded vessel.

6. The method of claim 1 further comprising determining characteristics of the fluid flowing through the vessel.

7. The method of claim 1 further comprising metallic reinforcement operably connected in combination with the polymer.

* * * * *